United States Patent [19]

Horrobin et al.

[11] Patent Number: 5,178,873
[45] Date of Patent: Jan. 12, 1993

[54] ESSENTIAL FATTY ACID TREATMENT

[75] Inventors: David F. Horrobin; Michael J. Finnen, both of Guildford, England

[73] Assignee: Efamol Holdings PLC, Surrey, England

[21] Appl. No.: 704,603

[22] Filed: May 23, 1991

[30] Foreign Application Priority Data

Jun. 6, 1990 [GB] United Kingdom ............... 9012651

[51] Int. Cl.⁵ ............ A61K 31/20; A61K 9/08; A61K 9/12; A61K 9/48
[52] U.S. Cl. .................................. 424/422; 424/45; 424/434; 424/435; 424/436; 424/451; 424/456; 424/463; 424/464; 424/489; 424/499; 424/427; 424/437; 514/560; 514/826; 514/861; 514/825; 514/886; 514/887
[58] Field of Search .............. 514/560, 826, 861; 424/422, 436

[56] References Cited

U.S. PATENT DOCUMENTS

| | | | |
|---|---|---|---|
| 4,584,320 | 4/1986 | Rubin | 514/826 X |
| 4,681,896 | 7/1987 | Horrobin | 514/861 X |
| 4,810,497 | 3/1989 | Horrobin | 514/560 X |
| 4,843,095 | 6/1989 | Rubin | 514/560 X |
| 4,855,136 | 8/1989 | Horrobin et al. | 514/560 X |
| 4,868,212 | 9/1989 | Horrobin | 514/861 X |
| 4,898,885 | 2/1990 | Horrobin | 514/560 |
| 4,977,187 | 12/1990 | Horrobin | 514/560 |

Primary Examiner—Paul R. Michl
Assistant Examiner—E. J. Webman
Attorney, Agent, or Firm—Nixon & Vanderhye

[57] ABSTRACT

A method of inhibiting phospholipase A2 in the control of inflammation, wherein delta-6,9,12,15-octadecatetraenoic acid (stearidonic acid) and/or delta-8,11,14,17-eicosatetraenoic acid is administered alone or in a pharmaceutically acceptable diluent or carrier.

8 Claims, No Drawings

ESSENTIAL FATTY ACID TREATMENT

FIELD OF THE INVENTION

This invention relates to inhibition of phospholipase A2 (PLA2) activity.

BACKGROUND

PLA2 is an enzyme which hydrolyzes fatty acids from the 2-position of phospholipids. Arachidonic acid (20:4 n-6, AA) is often present in substantial amounts at that position. AA bound to the phospholipid is not pro-inflammatory but once it has been released and is in the free form it can give rise to a wide variety of oxygenated derivatives which are produced by the activities of various enzymes including cyclo-oxygenase and 5-, 12- and 15-lipoxygenases. These derivatives include various prostaglandins, thromboxanes, leukotrienes and other compounds. Many of these AA derivatives play important roles in the promotion of inflammation.

In many circumstances inflammation is an appropriate physiological response to injury and other stimuli. However, all too often it becomes uncontrolled and instead of being beneficial produces both short term and long term damage. Examples of this are the various types of arthritis, of dermatitis, of asthma and of inflammatory bowel disease such as ulcerative colitis, among many others. Drugs which inhibit PLA2, notably the class of glucocorticoids, are usually potent antiinflammatory agents. The natural glucocorticoids and a whole array of synthetic and semi-synthetic derivatives are widely used orally, parenterally and topically on the skin, as aerosols, sprays or other forms of delivery for upper and lower respiratory passages; and as suppositories and other forms of rectally administered products for inflammatory disease of the bowel. However, although these drugs are used so widely they have many side effects and there is a considerable need for appropriate alternatives.

FATTY ACIDS

The pathways of conversion of the main series of polyunsaturated fatty acids in the body are as in Table 1 below:

TABLE 1

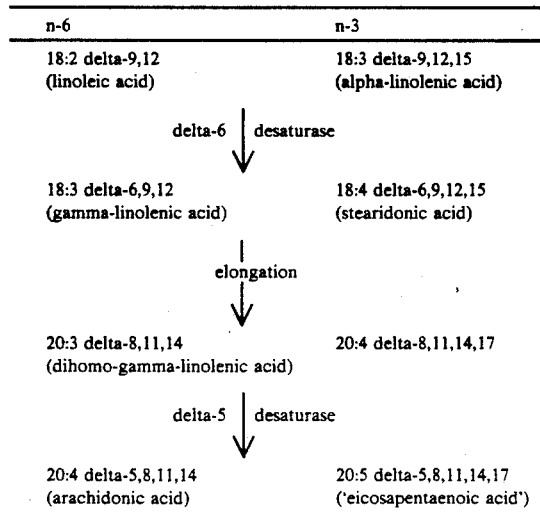

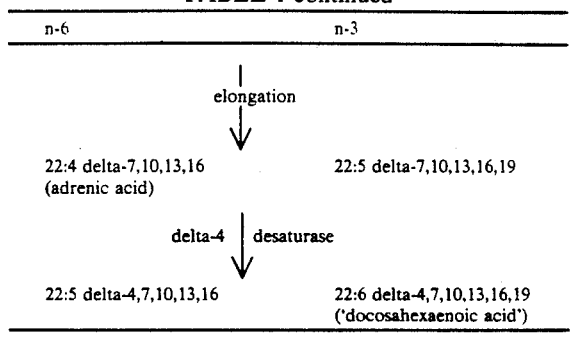

The above pathways are not normally reversible nor, in man, are n-3 and n-6 series acids interconvertible.

The acids, which in nature are of the all-cis configuration, are systematically named as derivatives of the corresponding octadecanoic, eicosanoic or docosanoic acids, e.g. delta-9,12-octadecadienoic acid or delta-4,7,10,13,16,19 docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

DISCUSSION OF THE INVENTION

We have recently been carrying out a series of observations on PLA2 isolated from human skin and from rat macrophages. The original idea behind the studies was that AA and other fatty acids released by PLA2 might give a feed back control of the activity of PLA2. We have found that this is indeed the case. More particularly and unexpectedly we have found that in both the test systems stearidonic acid (18:4 n-3, SA) is the most potent of all the fatty acids tested. Since, unlike AA and some of the other fatty acids which inhibit PLA2, SA cannot be converted to derivatives which have significant pro-inflammatory effects, our proposal is the use of SA as an agent which inhibits PLA2 and as an anti-inflammatory agent for oral, topical and parenteral use, including use in various types of systems which will deliver SA in effective amounts to the upper and lower respiratory tracts, to the bowel, and to other areas which may be inflamed such as the eyes, ears and joints. Further, since SA can be rapidly elongated in the body to 20:4 n-3 and administered SA may well be active in fact as 20:4 n-3, we also propose the use of this acid in the same way.

Of all the fatty acids which might inhibit PLA2, SA is particularly interesting, especially for its use in the skin. In general, the desaturation steps in the metabolism of unsaturated fatty acids are slow, while the elongation steps are rapid. The desaturation steps are completely absent in skin. SA may therefore rapidly be converted to 20:4 n-3, but only slowly converted onwards beyond that and in skin such onward conversion cannot occur at all. Neither SA nor 20:4 n-3 in itself is known to be converted to active metabolites which might have substantial pro-inflammatory actions. In both the test systems, AA was closest to SA in its ability to inhibit PLA2. However, AA would not be appropriate to use for its inhibitory effect because the AA itself could be converted to a range of pro-inflammatory metabolites. SA and 20:4 n-3 have in combination the ability to inhibit PLA2 and yet not being able themselves to give rise to pro-inflammatory substances such for example as prostaglandins arising from 20:5 n-3.

STATEMENT OF INVENTION

The invention provides in one aspect a method of manufacture of a medicament for the inhibition of phospholipase A2 in the control of inflammation, wherein delta-6,9,12,15-octadecatetraenoic acid (stearidonic acid) and/or delta-8,11,14,17-eicosatetraenoic acid is presented as said medicament alone or in a pharmaceutically acceptable diluent or carrier. Such control may, of course, be in either prevention or cure.

In another aspect the invention provides a method of inhibition of phospholipase A2 in the control of inflammation in a person suffering from or at risk of the same wherein a medicament comprising delta-6,9,12,15-octadecatetraenoic acid (stearidonic acid) and/or delta-8,11,14,17-eicosatetraenoic acid is administered in an effective amount to said person alone or in a pharmaceutically acceptable diluent or carrier.

The SA and 20:4 n-3 may be given along with other fatty acids or fatty acid glycerides as the diluent or carrier but desirably not in the presence of arachidonic acid. Since gamma-linolenic acid and dihomo-gamma-linolenic acids may themselves have anti-inflammatory properties there may be an advantage under some circumstances, especially in the skin, where it would be useful to combine these other acids with stearidonic acid. Conveniently the medicament is a topical preparation comprising 0.001 to 30%, preferably 0.1 to 5.0%, very preferably 0.5 to 3.0% of the or each said acid. Alternatively the medicament is in dosage unit form suited to oral, enteral, rectal, aerosol or parenteral administration of 1 mg to 50 g, preferably 10 mg to 10 g, very preferably 100 mg to 2 g per day. It may be delivered orally, enterally or rectally to the gastro-intestinal tract or by appropriate delivery methods to the respiratory tract, or parenterally.

FORMS AND SOURCES

SA and 20:4 n-3 can be made by chemical synthesis, or by enzyme conversion from alpha-linolenic acid (18:3 n-3), or by microbial techniques using fungi, algae or appropriately engineered bacteria. SA is also found in the oils of some plants, notably those derived from the seeds of the Ribes family, such as blackcurrant. SA from any source, whether or not mentioned here, can however be used in the invention.

SA and 20:4 n-3 can be used as the acid itself, or as appropriate derivatives such as salts, amides, esters, for example $C_1$ to $C_4$ alkyl esters and tri- and other glycerides, and phospholipids. Reference to the acids in the claims and else-where herein, is thus to be taken as including reference to such derivatives, which will deliver the acid to an appropriate part of the body and raise its concentration there.

Indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

DIETARY COMPOSITIONS

The invention is chiefly described in terms of methods of treatment and pharmaceutical compositions, but it will be understood that the gamma-linolenic and other EFAs, being in the nature of dietary supplements, can be incorporated in a dietary margarine or other foodstuff and such are to be understood as within the term pharmaceutical composition or medicament in the claims or elsewhere herein when for the purposes set out.

PHARMACEUTICAL PRESENTATION

Suitable compositions for pharmaceutical presentation are discussed in detail, for example, in Williams British Patent Specification No. 1,082,624, to which reference may be made, and are in any case very well known generally for any particular kind of preparation. Thus, for example, tablets, hard or soft gelatin or other capsules, enteric-coated capsules, ingestible liquid or powder preparations can be prepared as required, and topical preparations when the acids are to be absorbed through the skin or by other direct application. Injectable solutions may be prepared in various ways including the use of free albumin to solubilise free acids, or the preparation of lipid emulsions, or the use of water soluble salts such as the lithium or sodium salts.

Advantageously, a preservative is incorporated into the preparation. Alpha-tocopherol in concentration of about 0.1% by weight has been found suitable for the purpose and is one of a number of possible stabilisers well known in the field and including also for example ascorbyl palmitate and stearate.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXPERIMENTAL

In the experimental work on which the above discussion is based, epidermal PLA2 was prepared from isolated mouse or human epidermal cells by detergent solubilisation, ion exchange chromatography and gel filtration. Both enzymes had molecular weights in the region of 68,000, a pH optimum around 9.0 and an absolute requirement for calcium ions. Phospholipids were prepared as both unilamellar vesicles and detergent micelles. PLA2 activity was readily detected using these substrates, with no apparent preference for polar head group. For the standard assay, 1-palmitoyl 2-1-$^{14}$C. palmitoyl phosphatidyl choline was used. The reaction was initiated by the addition of purified enzyme and terminated by the addition of chloroform/methanol/acetic acid (3:4:1). The free fatty acid was extracted, separated by thin layer chromatography and quantified by scintillation counting. Ranges of concentrations of various fatty acids were added to the reaction mixture to assess their ability to inhibit PLA2. Dose response curves were constructed and the IC50 value (the concentration of fatty acid required to inhibit enzyme activity by 50%) was estimated. Similar experiments were performed using macrophages isolated from rat peritoneal cavity by lavage. The results are shown in Tables 2 and 3 below.

TABLE 2

IC50 values for the inhibition of human epidermal PLA2 activity by various fatty acids.

| | |
|---|---|
| 18:1 cis 6-octadecenoic | >100 μM |
| 18:2 cis 9,12-octadecadienoic (linoleic) | 85 ± 5 μM |
| 18:3 cis 6,9,12-octadecatrienoic (gamma-linolenic) | 52 ± 3 μM |
| 18:3 cis 9,12,15-octadecatrienoic (alpha-linolenic) | 45 ± 6 μM |
| 18:4 cis 6,9,12,15-octadecatetraenoic (SA) | 37 ± 3 μM |
| 20:1 cis 11-eicosenoic | >100 μM |
| 20:2 cis 11,14-eicosadienoic | 87 ± 6 μM |
| 20:3 cis 8,11,14-eicosatrienoic (dihomo-gamma-linolenic) | 61 ± 5 μM |
| 20:4 cis 5,8,11,14-eicosatetraenoic (AA) | 45 ± 8 μM |
| 20:5 cis 5,8,11,14,17-eicosapentaenoic (EPA) | 58 ± 4 μM |

TABLE 3

IC50 values for the inhibition of rat macrophage PLA2 activity by various fatty acids

| | |
|---|---|
| 18:1 cis 6-octadecenoic | >100 μM |
| 18:3 cis 9,12,15-octadecatrienoic (alpha-linolenic) | 75 ± 9 μM |
| 18:4 cis 6,9,12,15-octadecatetraenoic (SA) | 52 ± 8 μM |
| 20:1 cis 11-eicosenoic | >100 μM |
| 20:3 cis 8,11,14-eicosatrienoic (dihomo-gamma-linolenic) | 71 ± 11 μM |
| 20:4 cis 5,8,11,14-eicosatetraenoic (AA) | 65 ± 8 μM |

EXAMPLES

The following are administered for PLA2 inhibition in the treatment or prevention of inflammation: 1. A cream or ointment for topical use containing 1% of SA or 20:4 n-3, applied two to four times daily to affected areas of the body. 2. A cream or ointment for topical use containing 0.75% SA or 20:4 n-3, applied two to four times daily to affected areas of the body. 3. A fluid for rectal administration containing 2% SA or 20:4 n-3, administered two times daily, 50 ml on each occasion. 4. An aerosol for respiratory tract use containing 2% SA or 20:4 n-3, used four times daily to apply 4 mg of the acid on each occasion. 5. A parenteral injection for intravenous, intramuscular or intra-articular use containing 0.5 g of lithium-SA in 10 ml of an appropriate diluent, used at appropriate intervals as required, 1 to 5 ml on each occasion. 6. An emulsion for intravenous administration containing 0.5 g SA triglyceride in 10 ml, used at appropriate intervals as required. 7. Soft or hard gelatin capsules for oral administration, optionally enteric-coated, each containing 400 mg of SA, one to be taken four time a day. 8. Micro-granules made from starch or other appropriate material containing 20% by weight of SA triglyceride, 5 g to be taken three times per day. 9. Preparations as in Examples 1 to 8 additionally containing like amounts (to the SA or 20:4 n-3) of gamma-linolenic acid or dihomo-gamma-linolenic acid.

We claim:

1. A method of inhibiting phospholipase A2 in the control of inflammation comprising administering to a person suffering from same a phospholipase A2-inhibiting amount of delta-6,9,12,15-octadecatetraenoic acid.

2. A method of inhibiting phospholipase A2 in preventing inflammation comprising administering to a person at risk of the same a phospholipase A2-inhibiting amount of delta-6,8,12,15-octadecatetraenoic acid.

3. A method of claim 1 or 2 wherein from 1 mg to 50 g of delta-6,9,12,15-octadecatetraenoic acid is topically administered daily to the skin, bowel or respiratory tract.

4. The method of claim 3 wherein from 10 mg to 10 g of delta-6,9,12,15-octadecatetraenoic acid is topically administered per day.

5. The method of claim 1 or 2 wherein from 1 mg to 50 g per day of delta-6,9,12,15-octadecatetraenoic acid is orally, enterally or parenterally administered.

6. The method of claim 5 wherein from 10 mg to 10 g of delta-6,9,12,15-octadecatetraenoic acid is administered per day.

7. The method of claim 6 wherein from 100 mg to 2 g of delta-6,9,12,15-octadecatetraenoic acid is administered per day.

8. The method of claim 1 or 2 wherein gamma-linolenic acid or dihomo-gamma linolenic acid are also administered.

* * * * *